NEW AND DISTINCT VARIETY OF BLUEGRASS PLANT

Filed Sept. 17, 1970 2 Sheets-Sheet 1

NEW AND DISTINCT VARIETY OF BLUEGRASS PLANT

Filed Sept. 17, 1970 2 Sheets-Sheet 2

United States Patent Office

Plant Pat. 3,152

Patented May 2, 1972

3,152
NEW AND DISTINCT VARIETY OF BLUEGRASS PLANT

Gerard William Pepin, North Brunswick, and Cyril Reed Funk, Jr., Milltown, N.J., assignors to Rutgers University, New Brunswick, N.J.

Filed Sept. 17, 1970, Ser. No. 73,272
Int. Cl. A01h 5/00
U.S. Cl. Plt.—88 1 Claim

ABSTRACT OF THE DISCLOSURE

A Kentucky bluegrass plant having a wide plant spread and a dark, bluish-green color which is maintained from early spring to late fall. The plant is aggressive, highly apomictic and exhibits good resistance to stripe smut disease.

This invention relates to a new and distinct variety of bluegrass plant, the novel characteristics of which reside particularly in its very good horizontal spreading ability, a rich bluish-green color which is maintained throughout the growing season, and a highly aggressive turf.

The new variety was originated by us by crossing an unpatented selection identified in our breeding records as "Bellvue" with the cultivar "Pennstar," "Bellvue" being the seed parent and "Pennstar" being the pollen parent. As a result of this breeding, we have produced and asexually propagated by rhizomes, tillers and disseminules a new and improved variety which is distinct from each of its parents, as well as from all other varieties of which we are aware. The plants of the new variety were labeled "NJE P–106" Kentucky bluegrass.

NJE P–106 has exhibited at least the following desirable characteristics:

(1) Good rhizome and tiller development under turf maintenance, producing a high performance turf of excellent density and very good horizontal spreading ability;

(2) A very attractive, rich blue-green color which is maintained throughout the entire growing season;

(3) Good resistance to the strip smut disease incited by the fungus *Ustilago striiformis*;

(4) Good resistance to the leaf spot and crown rot disease incited by the fungus *Helminthosporium vagans*;

(5) Good resistance to the leaf rust disease incited by the fungus *Puccina poae-nemoralis*.

In comparison with its seed parent, Bellvue, the new variety has finer leaves, larger spikelets, a darker green color, maintains a more leafy turf during late spring, has better strip smut resistance, has better spreading ability, and exhibits higher turf performance.

In comparison with its pollen parent, Pennstar, the new variety has taller and more upright culms, fewer branches at the lowest node of the panicle, and better turf performance.

A primary object of the invention is to provide a new and distinct bluegrass plant having the desirable characteristics referred to above and to be described in detail below.

Other objects and advantages of the invention will become apparent from the following detailed description when taken in conjunction with the accompanying illustrations, in which.

Figure 1:
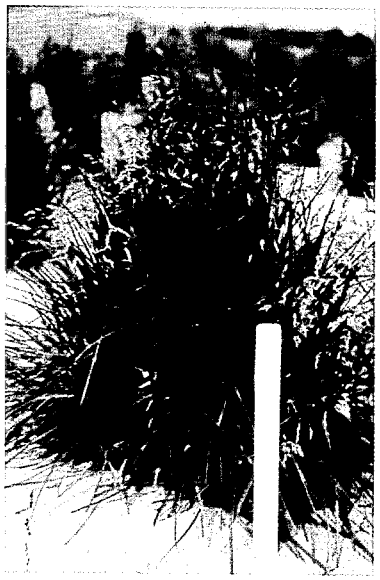
FIG. 1 shows a plant of the new variety shortly before the flowering stage.
Figure 2:
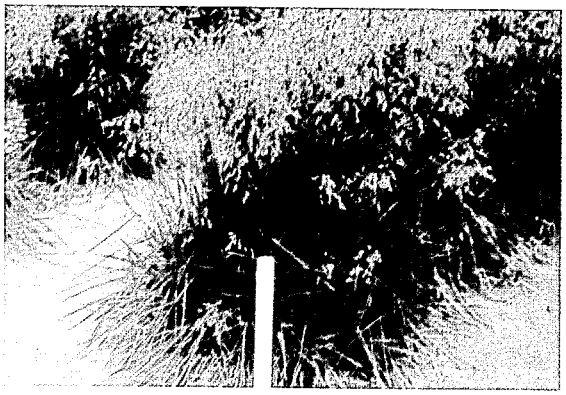
FIG. 2 shows a plant of the new variety under different lighting conditions after the completion of the flowering stage.
Figure 3:
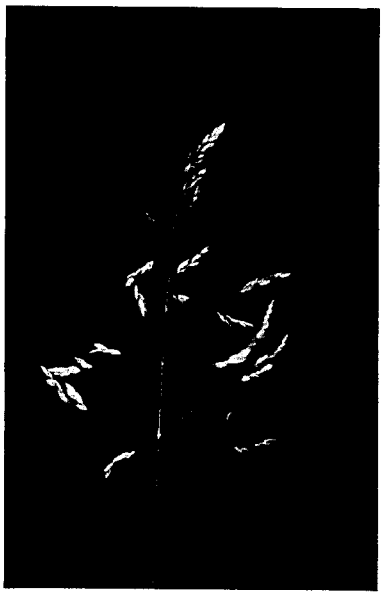
FIG. 3 shows a typical panicle of the new variety.
Figure 4:
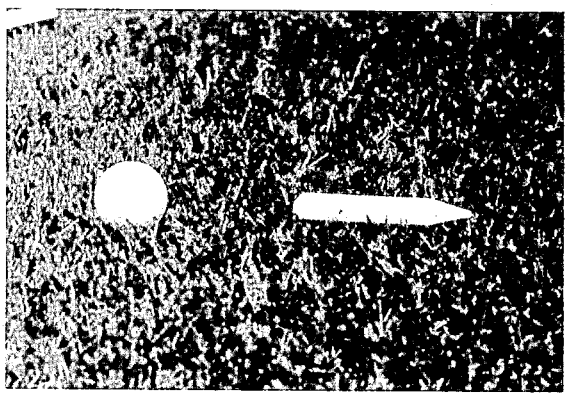
FIG. 4 shows a turf plot of the variety.

NJE P–106 is a perennial Kentucky bluegrass (*Poa pratensis*), but with a wider plant spread than most types belonging to this species. The plant is highly apomictic and has a moderate leaf texture, comparatively large spikelets, and a good quality turf. Of special moment is its good resistance to strip smut, leaf spot and leaf rust diseases.

PLANT DESCRIPTION

NJE P–106 Kentucky bluegrass has culms which initially are bent at the lowest nodes, later becoming mostly erect, tufted and average 62 to 68 cm. tall when undisturbed by clipping. The leaf blades are dark bluish-green in color and are from 3.5 to 5.0 mm. wide (average 3.7 mm.). The panicles average 79 to 102 mm. long and are pyramidal and open, with the lowermost branches in whorls of usually 3 or 4 (average 3.6). Spikelets ovate, compressed, 6 to 8 mm. long (average 7.1 mm.), 5 to 7 flowered (average 6.1), breaking up at maturity beneath each lemma. Glumes persistent, pointed, rough on the keels; lower ovate 3 to 4 mm. long (average 3.5 mm.), 1–3 nerved; upper ovate to elliptic, 3–4 mm. long (average 3.7 mm.), 3-nerved. Lemmas overlapping, ovate, oblong in side view, slightly pointed, 3 to 4 mm. long (average 3.5 mm.), pubescent on the lower half to two-thirds of keel and marginal nerves, with long fine crinkled hairs at the base, finely five-nerved, with thin tips and margins. Paleas about as long as the lemmas, with two rough keels. Caryopis enclosed by the hardened lemma and palea.

Since environmental conditions such as soil and climate influence morphological characteristics, these characteristics will vary somewhat under different conditions. The morphological characteristics of NJE P–106 and other Kentucky bluegrass varieties measured in 1970 at Adelphia, N.J., are shown in Table 1.

Table 1.—Morphological Comparison of NJE P–106 and Other Bluegrass Varieties

| Variety | Plant height, cm. | Plant diameter, cm. | Leaf blade width, mm. | Hairs on edge of collar [1] | Hairs on ligule [1] | Flag leaf length, mm. | No. of panicles per plant | Panicle color [2] | Panicle erect or nodding [3] | Number of branches at lowest panicle node | Panicle length, mm |
|---|---|---|---|---|---|---|---|---|---|---|---|
| NJE P–106 | 68 | 44 | 3.7 | 2.0 | 2.0 | 67 | 148 | 2.0 | 2.5 | 3.6 | 102 |
| Delta | 73 | 17 | 2.6 | 1.5 | 0.0 | 67 | 196 | 2.0 | 1.0 | 4.8 | 100 |
| Geary | 80 | 24 | 2.9 | 2.0 | 0.0 | 80 | 177 | 3.0 | 3.0 | 4.0 | 134 |
| Newport | 79 | 30 | 4.8 | 3.7 | 3.7 | 77 | 246 | 2.5 | 2.0 | 4.3 | 105 |
| Palouse | 79 | 24 | 3.0 | 1.0 | 0.0 | 93 | 151 | 3.0 | 3.5 | 4.4 | 92 |
| Anheuser Dwarf | 67 | 30 | 5.1 | 2.5 | 2.0 | 51 | 109 | 3.0 | 2.5 | 3.4 | 96 |
| Belturf | 70 | 35 | 3.0 | 2.0 | 1.0 | 58 | 201 | 2.0 | 2.0 | 4.0 | 104 |
| Fylking (Patent 2,887) | 60 | 34 | 4.0 | 1.5 | 1.5 | 68 | 164 | 3.5 | 5.0 | 4.9 | 118 |
| Merion | 70 | 24 | 4.3 | 3.5 | 0.5 | 69 | 280 | 2.0 | 1.5 | 3.5 | 102 |
| Pennstar | 59 | 34 | 3.7 | 2.2 | 1.0 | 66 | 132 | 3.5 | 4.0 | 4.5 | 106 |

[1] Scale: 0=no hairs; 5=most hairs.
[2] Scale: 0=green; 5=purple.
[3] Scale: 1=erect; 5=nodding.

CHARACTERISTICS OF CARYOPSIS

Caryopsis examination of NJE P–106 indicates the characteristics listed in Table 2.

TABLE 2.—CARYOPSIS CHARACTERISTICS OF NJE P-10

| | Character | Description |
|---|---|---|
| 1 | Intermediate nerves on lemma. | Generally indistinct, some exceptions. |
| 2 | Lemma color | Brownish, usually with darker base. |
| 3 | Lemma margins and apex | Wide hyaline margins, less flared and tapers to a long point; longer and markedly wider than palea. |
| 4 | Lemma texture | Granular. |
| 5 | In lateral plane—floret shape, plus thickness or plumpness. | Broadly lanceolate, tapering to longer point; short pointed base. Both palea and lemma sides arched. |
| 6 | Length | 3.0 to 4.0 mm. (average 3.25). |
| 7 | Width | 0.7 to 0.9 mm. (average 0.76). |

NJE P–106 has large seed, with one pound of Oregon produced seed containing approximately 1,138,000 seeds. For comparison, Merion is reported to produce about 2,000,000 seeds per pound, Windsor 1,521,000 seeds per pound and Common 1,600,000 seeds per pound.

CYTOLOGICAL CHARACTERISTICS

Studies of pollen mother cell meiosis indicate NJE P–106 has about 94 chromosomes. Root tip paraffin section of Bellvue, the female parent of NJE P–106, indicates about 56 chromosomes. Pennstar, the male parent of P–106, is reported to have about 76 chromosomes. NJE P–106 thus appears to be "triploid," combining all the chromosomes of Bellvue and about one-half the chromosomes of Pennstar.

REPRODUCTION AND PROPAGATION

Asexual reproduction of NJE P–106 by propagules (tillers and rhizomes) and disseminules (modified caryopses produced by agamospermy) has constantly produced progeny plants indistinguishable from the mother plant.

TURF CHARACTERISTICS

Overall turf performance ratings for NJE P–106 and other bluegrasses for the years 1966 through 1970 at New Brunswick, N.J., are listed in Table 3.

TABLE 3.—TURF PERFORMANCE RATINGS OF NJE P-106 AND OTHER BLUEGRASS VARIETIES

| | Turf performance score (10=best) | | | | | |
|---|---|---|---|---|---|---|
| Variety | 1966 | 1967 | 1968 | 1969 | 1970 | Average |
| NJE P-106 | 7.9 | 7.6 | 8.5 | 8.6 | 8.0 | 8.1 |
| Bellvue | 6.4 | 6.7 | 6.9 | 5.9 | 5.7 | 6.3 |
| Anheuser Dwarf | 7.6 | 7.3 | 7.5 | 6.9 | 7.6 | 7.4 |
| Pennstar | 6.9 | 6.8 | 7.9 | 7.1 | 7.2 | 7.2 |
| Fylking | 6.9 | 6.8 | 8.0 | 7.6 | 7.2 | 7.3 |
| Belturf | 6.2 | 5.9 | 7.4 | 7.0 | 6.2 | 6.5 |
| Merion | 6.3 | 6.1 | 6.8 | 4.9 | 4.1 | 5.6 |
| Delta | 4.5 | 4.2 | 5.2 | 4.9 | 4.5 | 4.7 |
| Windsor | 5.0 | 5.0 | 6.4 | 5.4 | 4.3 | 5.2 |

The new variety has exhibited consistently high turf performance ratings. Of particular significance is its high sod strength and good aggressiveness, as shown by Tables 4 and 5.

TABLE 4

Sod strength of NJE P–106 and other bluegrass varieties ten months after seeding

| Variety: | Pounds tension required to separate a 12-inch piece of sod |
|---|---|
| NJE P–106 | 59 |
| Merion | 36 |
| Kenblue | 27 |
| Park | 27 |
| Newport | 19 |
| Windsor | 18 |
| Common (South Dakota Certified) | 8 |

TABLE 5

Aggressiveness of various bluegrass varieties as measured by their ability to spread under conditions of close mowing and competition from other bluegrasses (1970)

| Variety: | Amount of encroachment into adjacent bluegrass varieties (inches) |
|---|---|
| NJE P–106 | +10.0 |
| Belturf | +8.0 |
| Bellvue | +3.0 |
| Pennstar | +2.5 |
| Fylking | +2.5 |
| Anheuser Dwarf | +2.0 |
| Merion | −1.5 |
| Windsor | −1.5 |
| Delta | −3.0 |

DISEASE RESISTANCE

A comparison of NJE P–106 and other bluegrass varieties for resistance to stripe smut caused by the fungus *Ustilago striiformis*, leaf spot caused by the fungus *Helminthosporium vagans*, and leaf rust caused by the fungus *Puccinia poae-nemoralis* is given in the following tables:

TABLE 6

Relative comparison of stripe smut disease resistance for NJE P–106 and other bluegrasses at New Brunswick, N.J.

| Variety: | Stripe smut infected tillers per square foot |
|---|---|
| NJE P–106 | *1 |
| Bellvue | 11 |
| Pennstar | *0 |
| Anheuser Dwarf | *0 |
| Fylking | *0 |
| Belturf | *2 |
| Merion | 228 |
| Delta | 11 |
| Windsor | 41 |

NOTE.—Values maked (*) do not differ significantly at the 5% probability level.

TABLE 7.—RELATIVE COMPARISON OF LEAF SPOT DISEASE FOR NJE P-106 AND OTHER BLUEGRASSES AT NEW BRUNSWICK, N.J., IN 1970

| | Percent leaf spot damage | |
|---|---|---|
| Variety | 1968 planting | 1967 planting |
| NJE P-106 | 3 | 5 |
| Pennstar | 5 | 6 |
| Fylking | 5 | 6 |
| Belturf | 13 | 20 |
| Merion | 5 | 5 |
| Delta | 81 | 80 |
| Windsor | 47 | 25 |
| Park | 84 | 85 |
| Kenblue | 89 | 90 |
| Common (South Dakota Certified) | 92 | 95 |

TABLE 8

Relative comparison of leaf rust disease level for NJE P–106 and other bluegrass varieties at New Brunswick, N.J., in 1970

| Variety: | Rust disease rating [1] |
|---|---|
| NJE P–106 | 1.5 |
| Pennstar | 1.5 |
| Fylking | 1.5 |
| Prato | 2.0 |
| Geary | 3.0 |
| Newport | 3.5 |
| Merion | 3.5 |

[1] Scale: 0=no rust; 9=most disease.

These tests indicate that NJE P–106 has good resistance to stripe smut, leaf spot and leaf rust diseases.

It will be apparent from the foregoing that the new variety has demonstrated excellent turf performance, with high sod strength and good aggressiveness. The turf exhibits a rich dark blue-green color and has a moderate leaf texture. The plant has a wide spread, large spikelets and good rhizome and tiller development.

What is claimed is:

1. A new and distinct variety of Kentucky bluegrass plant, substantially as herein shown and described, characterized particularly by excellent turf performance, a rich, dark blue-green color, good rhizome and tiller development, large spikelets, and a wide plant spread.

No references cited.

ROBERT E. BAGWILL, Primary Examiner